United States Patent [19]

Sletzinger

[11] 4,337,360
[45] Jun. 29, 1982

[54] PROCESS FOR PREPARING METHYLVANILLYL KETONE FROM ISOEUGENOL

[75] Inventor: Meyer Sletzinger, North Plainfield, N.J.

[73] Assignee: Merck & Co., Inc., Rahway, N.J.

[21] Appl. No.: 79,748

[22] Filed: Sep. 28, 1979

[51] Int. Cl.$^3$ ............................................. C07C 45/42
[52] U.S. Cl. .................................. 568/322; 560/254; 549/525; 549/526; 549/561
[58] Field of Search .......... 260/590 R, 590 E, 348.25; 568/322; 560/254

[56] References Cited

U.S. PATENT DOCUMENTS

4,169,858 10/1979 Gal et al. ............................. 568/822
4,230,893 10/1980 Gal ...................................... 568/822

OTHER PUBLICATIONS

Suga et al., Chem. Abst., vol. 77, #1139425 (1972).
Freudenberg et al., Chem. Ber., vol. 76, pp. 997–1006 (1943).
Kulka et al., J.A.C.S., vol. 65, pp. 1180–1185 (1943).

Primary Examiner—Natalie Trousof
Assistant Examiner—James H. Reamer
Attorney, Agent, or Firm—Salvatore C. Mitri; Daniel T. Szura

[57] ABSTRACT

Methylvanillyl ketone is prepared from a "through process" involving oxidation of isoeugenol followed by subsequent acidic hydrolysis.

4 Claims, No Drawings

PROCESS FOR PREPARING METHYLVANILLYL KETONE FROM ISOEUGENOL

BACKGROUND

This invention relates to a new, alternate process for preparing methylvanillyl ketone (MVK), or 4-hydroxy-3-methoxyphenylacetone, which is a useful intermediate for the synthesis of methyldopa, one of the most important antihypertensive agents.

The use of MVK in the methyldopa process has been disclosed in U.S. Pat. No. 2,868,818 which comprises the addition of a cyanide anion to MVK to form 4-methyl-4-(4-hydroxy-3-methoxybenzyl)hydantoin followed by basic hydrolysis to form α-methyl-β-(4-hydroxy-3-methoxyphenyl)alanine. Subsequent acidic hydrolysis produces methyldopa, i.e., α-methyl-β-(3,4-dihydroxyphenyl)alanine.

Presently, MVK is manufactured from vanillin and nitroethane [Kulka et al, *J. Am. Chem. Soc.*, 65, 1184 (1943)]. However, this process suffers from the high cost of vanillin and the fact that there is only one supplier for nitroethane.

For these reasons, an alternate process for the production of MVK is desirable to safeguard the continuous production of methyldopa.

The novel process of the present invention concerns the direct oxidation of unprotected isoeugenol to form a glycol intermediate followed by subsequent acidic conversion to MVK. Although the process includes two chemical reactions, it is virtually a single-step "through process". MVK is the first and only isolated product.

The peroxide-oxidation of a protected isoeugenol, i.e., acetyl isoeugenol, to form an epoxide precursor of MVK is known (K. Freudenberg et al, *Chem. Ber.*, 76, pp. 1005–1006, 1943). However, Freudenberg et al's process is not a "through process". It involves three steps, all of which require the isolation of products. It also suffers from low yield (30%).

Moreover, the novel process of this invention is distinguishable from Freudenberg et al's process. First, as will be shown later in Equation A, the present process oxidizes unprotected isoeugenol to generate a glycol intermediate instead of an epoxide. Second, the glycol intermediate generated does not come from the hydrolysis of a preceding epoxide. The epoxide simply does not exist due to the presence of a free phenol group in isoeugenol.

Therefore, it is an object of the present invention to provide a new, alternate process for the production of methylvanillyl ketone from isoeugenol.

It is also an object of this invention to provide a process which is economically more advantageous than the current vanillin process for the manufacturing of MVK.

Still another object of this invention is to provide a "through process" for preparing MVK which requires no isolation of products before that of MVK and thus is simpler, shorter, and more efficient than Freudenberg et al's synthesis.

DETAILED DESCRIPTION OF THE INVENTION

The present invention concerns a new, alternate process for the production of methylvanillyl ketone (MVK). The process can be represented as follows.

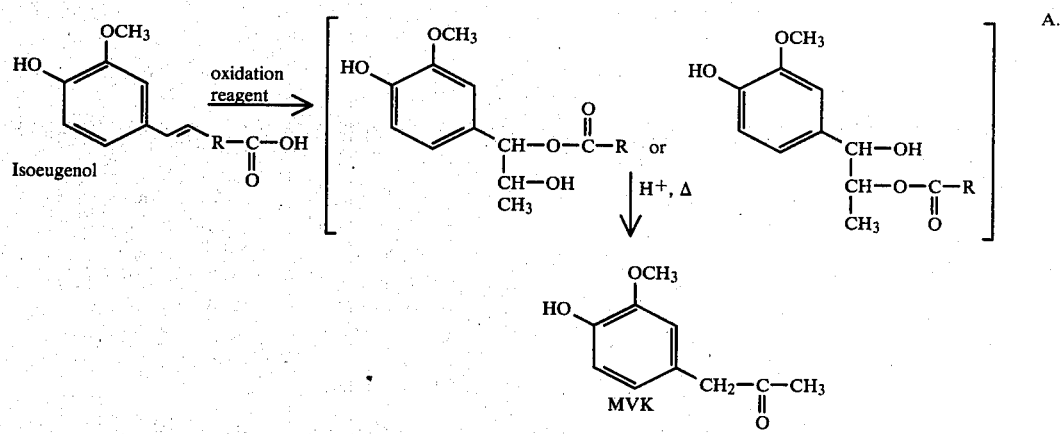

wherein R is hydrogen, $C_{1-5}$ alkyl especially methyl, ethyl, propyl, butyl or amyl, trifluoromethyl or trichloromethyl; and the oxidation reagent is peroxide such as hydrogen peroxide or disuccinoyl peroxide, peracid such as performic acid, peracetic acid, peroxytrifluoroacetic acid, monopersuccinic acid, m-chloroperbenzoic acid, p-methoxycarbonylperbenzoic acid, O-sulfoperbenzoic acid or monoperphthalic acid, or other oxidation reagents such as iodine-silver oxide, iodine-mercuric oxide, N-bromosuccinimide-perchloric acid, or thallium triacetate.

The oxidation is usually conducted in an aqueous solution of an organic acid such as formic, acetic, propionic, trichloroacetic, or trifluoro acetic acid. The formic acid and acetic acid generally give better results. The preferred oxidation reagents are hydrogen peroxide and peracetic acid. The most preferred embodiment is the combination of hydrogen peroxide and formic acid. The oxidation generally requires mild heating at about 25° C.–100° C., preferably at 30° C.–60° C., for about 1–6 hours or until the reaction is substantially complete. If hydrogen peroxide and formic acid are used at 35° C.–40° C., the reaction is substantially complete in about 2.5 hours or less.

The in situ conversion of the resulting glycol monoester without isolation to MVK is accomplished by heating the reaction mixture together with an aqueous solution of a strong acid and an inert solvent such as benzene, toluene or xylene. The strong acid used is usually sulfuric, alkyl or aryl sulfonic, hydrobromic, hydrochloric or phosphoric acid.

Preferably, a sufficient amount of 10%–20% aqueous sulfuric acid and toluene is added to the reaction mixture and the entire mixture is heated to reflux until the reaction is substantially completed. Under the preferred conditions, the reaction time ranges from 6–16 hours.

Another embodiment of the present invention is a novel improvement of the Freudenberg et al process which involves the oxidation of acetyl isoeugenol with perbenzoic acid in chloroform followed by acid treatment to give a 30% yield of MVK. The improved process, however, uses peracetic acid or other oxidation reagents in an acidic medium such as an alkanoic acid for the initial oxidation. This modification eliminates all the isolations of intermediates required by Freudenberg et al. As a result, the over-all yield of MVK unexpectedly increases from Freudenberg et al's 30% to 85%. The improved process can be represented as follows:

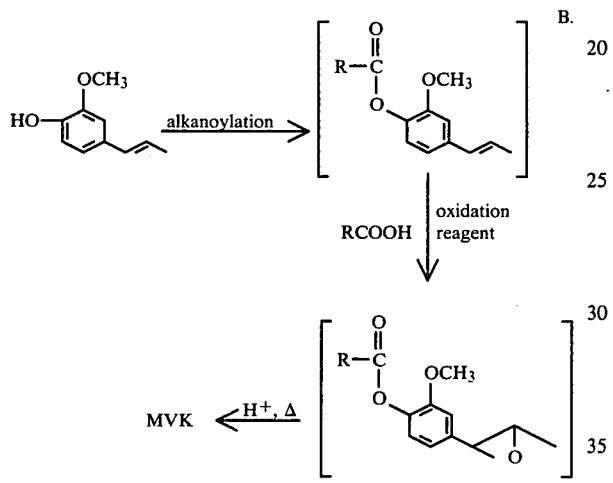

B.

wherein R and the oxidation reagent are as previously described.

The improved method is also a single-step "through process". After isoeugenol is protected by alkanoylation such as acetylation in acetic anhydride and sodium acetate or butanoylation with butynylchloride, the reaction mixture is diluted with an inert solvent such as toluene, xylene or benzene and treated directly with peracetic acid or other oxidaton reagents as previously described. Following mild heating at about 25° C.–100° C., preferably about 50° C.–60° C. for about 1–6 hours, the substantially complete reaction is quenched with aqueous sodium sulfite to destroy excess oxidation reagent. When peracetic acid is used, the oxidation is essentially complete within 2–3 hours. The resulting alkanoyl isoeugenol epoxide is converted in situ to MVK upon heating with a strong acid in an inert solvent as described previously in Equation A.

It is essential to eliminate any isolation of intermediates before the last step. As illustrated by Examples 2 and 3, the yield for the "through process" is 85% (Example 2) while the yield from stepwise process (Example 3) drops to 54%.

EXAMPLE 1

Methylvanillyl Ketone (MVK) from Isoeugenol

A solution of 30% aqueous hydrogen peroxide (9 ml, 85.5 mm) and formic acid (16 ml, 88%) is added to a solution of isoeugenol (8.1 gm, 50 mm) in formic acid (4 ml). The reaction mixture is stirred at 35° C.–40° C. under nitrogen atmosphere for 3 hours. The resulting 1-(4-hydroxy-3-methoxyphenyl)-propane-1,2-diol-monoformate is treated with 10% aqueous sulfuric acid (125 ml.) and toluene (125 ml.). After refluxing with mixing for 6 hours, the reaction mixture is cooled to room temperature, and the toluene layer separated. The aqueous layer is extracted with fresh toluene and the toluene layers are combined, washed with saturated aqueous sodium sulfate, dried over anhydrous sodium sulfate and concentrated to give methylvanillyl ketone in 48% yield.

EXAMPLE 2

Methylvanillyl Ketone from Acetyl Isoeugenol
(Through Process)

A mixture of isoeugenol (8.21 g., 50 mm.), acetic anhydride (5.62 g., 55 mm.) and anhydrous sodium acetate (0.41 g., 5 mm.) is heated at 100° C.–105° C. under nitrogen atmosphere for 2.5 hours. The reaction mixture is cooled and diluted with 65 ml. of toluene before a solution (11 ml.) of 38.6% peracetic and 0.85 g. of sodium acetate in acetic acid is added slowly. After heating at 50° C.–60° C. for 2–3 hours, the reaction mixture is cooled to 20° C. and treated with aqueous sodium bisulfite (2.8 g.) to destroy excess peracetic acid. The entire mixture is mixed with 8 ml. of toluene, 50 ml. of 14% aqueous sulfuric acid, and is heated with stirring to reflux for 12.5 hours. After cooling to ambient temperature, the toluene layer is separated, and the aqueous layer extracted 3×20 ml. of toluene. The toluene layers are combined, washed with saturated aqueous sodium sulfate, dried over anhydrous magnesium sulfate and concentrated in vacuo to give methylvanillyl ketone in 85.3% yield.

EXAMPLE 3

Methylvanillyl Ketone from Acetyl Isoeugenol
(Stepwise Process)

Step (a): Preparation of Acetyl Isoeugenol

To a solution of isoeugenol (344 g., 2.1 moles) in 420 ml. of pyridine under nitrogen atmosphere is added 428 ml. of acetic anhydride over a period of 30 minutes. The resulting solution is stirred at room temperature overnight followed by treatment with ice-water (1400 ml.). After stirring for three hours, the resulting precipitate is filtered, washed with water (3×500 ml.) and dried in vacuo to give 381.7 g. of crude product. Acetyl isoeugenol (269 g., 62%) is obtained from washing the crude product with n-hexane.

Step (b): Preparation of Acetyl Isoeugenol Epoxide

To a solution of acetyl isoeugenol in 65 ml. of toluene under nitrogen atmosphere is added a solution of 38.6% peracetic acid (11 ml.) followed by addition of 0.85 g. of sodium acetate. The reaction mixture is stirred and heated at 50° C.–62° C. for 2.5 hours before it is cooled and quenched with aqueous sodium bisulfite (2.89 g. in 8 ml. of cold water). The crude product so obtained is directly used in the next step.

Step (c): Preparation of methylvanillyl Ketone

To the crude product from step (b) is added 10% aqueous sulfuric acid (50 ml.). The reaction mixture is stirred and heated at reflux for 12.5 hours. After cooling to room temperature, the toluene layer is separated and the aqueous layer is extracted with 3×20 ml. toluene. The combined toluene layers are dried over magnesium sulfate, filtered, and evaporated in vacuo to give methylvanillyl ketone in 54% over-all yield based on isoeugenol.

I claim:

1. A through process for preparing methylvanillyl ketone which comprises:
   (1) oxidation of a protected isoeugenol in a dilute, inert solvent to obtain a reaction mixture containing protected isoeugenol epoxide as an intermediate therein;
   (2) treating said reaction mixture with a strong acid in an inert solvent; and
   (3) recovering methylvanillyl ketone directly from said acid-treated reaction mixture without isolating said protected isoeugenol epoxide intermediate.

2. The process of claim 1 wherein the oxidation reagent is peroxide or peracid and the protected isoeugenol is an alkanoyl isoeugenol.

3. The process of claim 2 wherein said alkanoyl group is acetyl, the oxidation reagent is peracetic acid, peroxytrifluoroacetic acid, performic acid, or hydrogen peroxide; the strong acid is 10%–20% aqueous sulfuric acid; and the inert solvent is toluene or xylene.

4. The process of claim 3 wherein the peroxide is peracetic acid; the strong acid is 14% aqueous sulfuric acid; and the solvent is toluene.

* * * * *